(12) United States Patent
Barhak (10) Patent No.: US 9,858,390 B2
(45) Date of Patent: Jan. 2, 2018

(54) REFERENCE MODEL FOR DISEASE PROGRESSION

(71) Applicant: Jacob Barhak, Austin, TX (US)

(72) Inventor: Jacob Barhak, Austin, TX (US)

(*) Notice: Subject to any disclaimer, the term of this patent is extended or adjusted under 35 U.S.C. 154(b) by 356 days.

(21) Appl. No.: 14/091,353

(22) Filed: Nov. 27, 2013

(65) Prior Publication Data

US 2014/0297241 A1 Oct. 2, 2014

Related U.S. Application Data

(60) Provisional application No. 61/806,365, filed on Mar. 28, 2013.

(51) Int. Cl.
G06F 19/00 (2011.01)

(52) U.S. Cl.
CPC ............... *G06F 19/3437* (2013.01)

(58) Field of Classification Search
CPC ............ G06F 19/3437; G06F 19/345; G06F 19/3431; G06F 17/50; G06F 17/5009; G06F 19/00; G06F 19/26; G06F 19/321; G06F 19/325; G06F 19/3443; G06F 19/12; G06F 19/24; G06F 19/28; G06F 19/322; G06F 19/3481
USPC ........ 703/6; 707/999.103, 999.005, 999.004, 707/999
See application file for complete search history.

(56) References Cited

U.S. PATENT DOCUMENTS

| | | | | |
|---|---|---|---|---|
| 6,108,635 A | * | 8/2000 | Herren | G06F 19/322 600/300 |
| 6,234,964 B1 | * | 5/2001 | Iliff | G06F 19/322 600/300 |
| 8,691,232 B2 | * | 4/2014 | Derynck | A61K 39/395 424/138.1 |
| 9,109,256 B2 | * | 8/2015 | Shuber | C12Q 1/6886 |
| 9,141,756 B1 | * | 9/2015 | Hillis | G06F 19/12 |
| 9,689,826 B2 | * | 6/2017 | Haick | G01N 27/26 |
| 2006/0188509 A1 | * | 8/2006 | Derynck | A61K 39/395 424/155.1 |
| 2009/0155259 A1 | * | 6/2009 | Derynck | A61K 39/395 424/133.1 |
| 2011/0165157 A1 | * | 7/2011 | Derynck | A61K 39/395 424/133.1 |
| 2014/0257047 A1 | * | 9/2014 | Sillay | A61B 5/11 600/301 |
| 2015/0273059 A1 | * | 10/2015 | Derynck | A61K 39/395 424/450 |
| 2016/0041153 A1 | * | 2/2016 | Brown | G01N 33/5308 435/7.23 |
| 2016/0300036 A1 | * | 10/2016 | Ramazzotti | G06F 19/12 |

* cited by examiner

*Primary Examiner* — Sheree N Brown (74) *Attorney, Agent, or Firm* — Lee & Hayes, PLLC (57) ABSTRACT

A method wherein reference disease models predict progression of disease within given populations, utilizing publically available clinical data and risk equations, to give a birds-eye view of clinical trials by allowing multiple trials to be systematically compared simultaneously via parallel processing/High Performance Computing which allows competition among alternative equations/hypothesis combinations; cross validation; and, then ranks results according to fitness via a fitness engine.

20 Claims, 5 Drawing Sheets

REFERENCE MODEL FOR DISEASE PROGRESSION

This application claims priority over, and incorporates by reference in its entirety, U.S. Provisional Application 61/806,365 filed on Mar. 28, 2013.

FIELD OF USE

The present invention relates to a computer model in which disease progression is calculated within given populations.

BACKGROUND OF THE INVENTION

Prior approaches to disease progression analysis use complex proprietary data, while the present invention utilizes publically available data and does not require access to any proprietary data.

U.S. patent application Ser. No. 11/503,393 (David Eddy, et al.) discloses a method for simulating a clinical trial includes: selecting a trial procedure for a simulated trial corresponding to the clinical trial; generating a population of subjects for the simulated trial; searching the population of subjects to determine acceptable subjects for the simulated trial; selecting subjects for the simulated trial from the acceptable subjects; simulating the trial procedure for the selected subjects; and collecting trial data for the simulated trial from the simulated trial procedure.

U.S. patent application Ser. No. 12/788,242 (David Eddy, et. al.) discloses a method of determining a quality of care provided by a healthcare provider to individuals in a population is provided. A data processing apparatus that has one or more processors is disclosed. Data representing biomarkers for individuals in a population is received. Baseline and present risks are determined. Risk reduction values are determined. Based on the current risk reduction, a quality score is determined. A scale is created, and the quality score is mapped to the scale. The global quality score of the disclosure provides numerous benefits over past performance measures.

U.S. Pat. No. 8,224,665 (Macdonald Morris) discloses a method and apparatus for predicting a health benefit for an individual is provided. Outcomes from a first simulation on a set of simulated individuals reflecting a population are stored and used to determine a first risk function and corresponding cost values. Outcomes from a second simulation on a set of simulated individuals reflecting having a healthcare intervention are stored and used to determine a second risk function reflecting the intervention and corresponding cost values of the intervention. A benefit function is derived from the difference of the first and second risk functions. A cost function that describes the cost of the intervention is derived from the respective cost values. The derived benefit function and cost function are used to predict the corresponding benefit and cost of the healthcare intervention for a given individual. Individuals can be ranked by degree of expected benefit.

The Cardiff Model discloses a method to evaluate the impact of new therapies in a population of T2DM patients, modeling disease progression through the implementation of the UK Prospective Diabetes Study (UKPDS) 68 outcomes equation with the model requiring specification of: age, sex, ethnicity, smoking status and duration of diabetes and model changes to the following modifiable risk factors: total cholesterol, HDL cholesterol, systolic blood pressure, weight and glycosylated hemoglobin (HbA1c). While the time-dependent risk factor profiles are simulated through implementation of equations reported in the UKPDS 68 study, pre-specified HbA1c threshold values may be used to invoke escalation to second- and third-line therapies with costs applied to all predicted complications in the year of occurrence. Healthcare maintenance costs are applied in all subsequent years following non-fatal events with the costs of diabetes-related complications being drawn primarily from UKPDS 65 while baseline utility is modeled using age-dependent mean EQ-5D values in subjects, obtained from the Health Survey for England 2003, with no major complications. Utility decrements associated with predicted complications are drawn primarily from UKPDS 62 with model output including: micro-vascular: retinopathy, neuropathy, nephropathy; and macro-vascular complications: congestive heart failure, myocardial infarction, stroke, ischaemic heart disease; hypoglycaemia, diabetes-specific mortality, all-cause mortality and point estimates, and probabilistic output for cost-effectiveness.

The CDC-RTI Diabetes Cost-Effectiveness Model discloses a method of disease progression and cost-effectiveness for type 2 diabetes, following patients from diagnosis to either death or 95 years of age. The model simulates development of diabetes related complications on three micro-vascular disease paths (nephropathy, neuropathy, and retinopathy) and two macro-vascular disease paths for diabetes screening and pre-diabetes with model outcomes including: disease complications, deaths, costs, and quality-adjusted life years. In the model, progression between disease states is governed by transition probabilities that depend on risk factors—including glycemic level (measured by HbA1c levels), blood pressure, cholesterol, and smoking status—and the duration of diabetes. Interventions affect the transition probabilities and resulting complications. For example, tight glycemic control lowers HbA1c, slowing progression on the micro-vascular complication paths. With slower progression, fewer micro-vascular complications occur, resulting in death being delayed, QALYs increase, with the resulting cost of complications reduced. The model has been used to estimate the cost-effectiveness of treatment interventions for patients with diagnosed diabetes while evaluating optimal resource allocation across interventions; assess whether screening for diabetes is cost-effective; show that lifestyle modification is cost-effective in delaying or preventing diabetes among persons with pre-diabetes; and estimate the cost-effectiveness of screening for pre-diabetes.

The Diabetes and Analysis Modeling Framework model uses established methods to develop the central simulation engine (CSE) that lies at the nucleus of DMAF. The architecture of DMAF has been designed so emerging evidence reported in the literature can be efficiently incorporated into the framework and evaluated for potential impact on immediate and long term outcomes. DMAF captures events occurring in routine patient care through an A1c sub model, bridging between patient-specific A1c, and the incidence of complications while multiplicative factors are taken from A1c vs. time curves from published head-to-head studies of the treatments considered. DMAF also contains treatment transition and scheduling based, by default, the treatment consensus algorithm published by Nathan et al. The transitions between treatment strata are modifiable for sensitivity analysis including the functionality to randomly sample a range of start times for additional treatment.

Disease models predict disease progression within a population. Yet, predictions differ among models and populations while models become outdated and do not account for improvement in treatment and newer medical advances.

Modeling treatment improvement on top of existing models is highly beneficial, while, to a lesser extent, including biomarker change is also beneficial; including both improvements together, i.e. treatment improvement and biomarker change, improves models in many cases.

The Reference Model is currently based on secondary data published in clinical trials, with published risk equations, while no individual data is necessary. Yet it is possible to use individual data and non published risk equations with the model. The use of public data the model uses does not limit it.

SUMMARY OF THE INVENTION

A primary purpose of The Reference Model for disease progression is to facilitate a model systematic performance comparison over multiple populations and produce fitness information while also allowing testing hypothesis, for example two hypotheses can be tested: Medical treatment improved through time beyond model prediction, and how the biomarker change improves model predictions.

While disease models predict disease progression within a population, predications differ among models and populations, and because models become outdated, they do not account for improvement in treatment and newer medical advances. Because of this, they should periodically be updated or include a temporal correction term for treatment improvement.

The Reference Model is built from publically available data, using MIST (Micro-Simulation Tool)—a Python based modeling framework which is available under Genaral Public License (GPL), and does not require access to proprietary, or indivtual patient, information. The software uses Monte Carlo simulations that are executed in parallel, and in the data shown in this application, the system can run on a single machine, on a cluster of machines, and on a cluster in the cloud. With the model utilizing computer power/techinques, such as parallel processing/high performance computing, cross validation, competition among alternative equations and/or hypotheses combinations, and ranks results based on fitness via a fitness engine multiple studies can be compared and large amounts of study data, which was unaccessable before, is now available to determine disease progression over large populations comprising large data sets.

While further areas of applicability will become apparent from the description provided herein, the following description, examples and drawings are shown by way of example, and in no way limit the scope of the present disclosure.

DETAILED DESCRIPTION OF THE PREFERRED EMBODIMENTS

Figure 1:
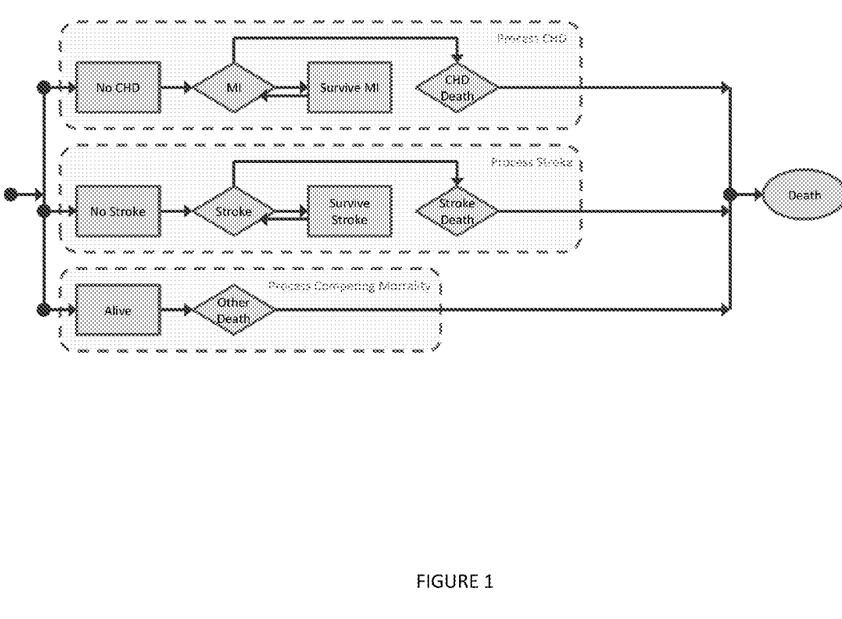
FIG. 1 depicts a block diagram of The Reference Model.

FIG. 1, is an example of a multi-process state transition model that forms a base for The Reference Model. In this particular example, the processes are: process CHD (coronary heart disease), process stroke, and process competing mortality. In the CHD process, the population data is entered to the appropriate state, during simulation, a healthy individual first goes through the no CHD state, next depending on the risk equation chosen and Monte Carlo random factors, the individual may flow into the MI (Myocardial Infarction) event state that filters individuals with those who died and survived are further separated. The same process occurs for the other disease states, in this particular case, stroke and competing mortality, which is those who died from something other than two processes being compared, which in this case are deaths from heart disease and stroke.

Figure 2:
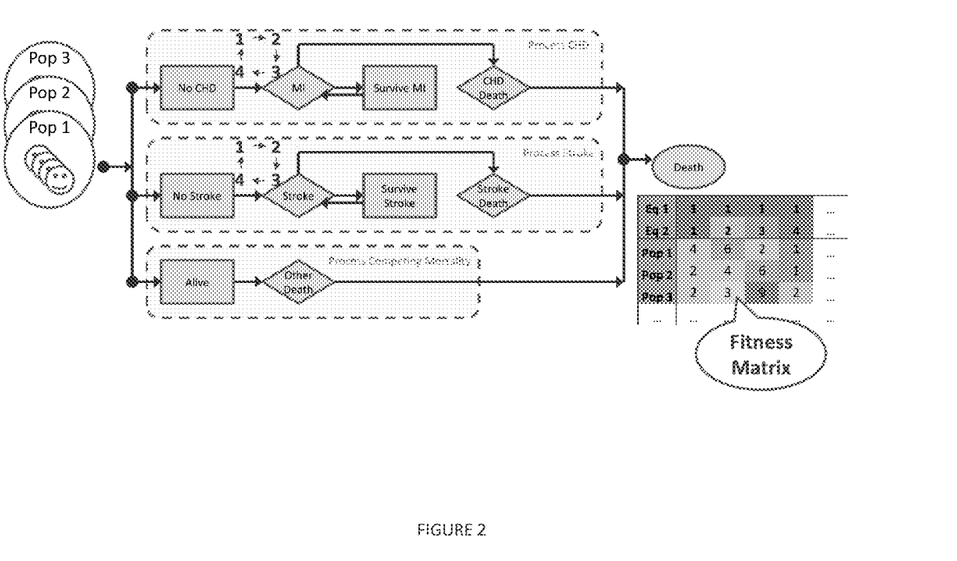
FIG. 2 depicts a block diagram of The Reference Model and how it functions.

FIG. 2, shows an outline of how The Reference Model works. Multiple populations enter the model depicted in FIG. 1, then different risk equations are applied to different transitions to modify model behavior. In this example 4 equations are used for MI and 4 equations are used for stroke. Once this data has been analyzed for all individuals in all populations and for all risk equations, the fitness matrix is then produced, which depicts difference of the simulation from observed outcomes.

Figure 3:
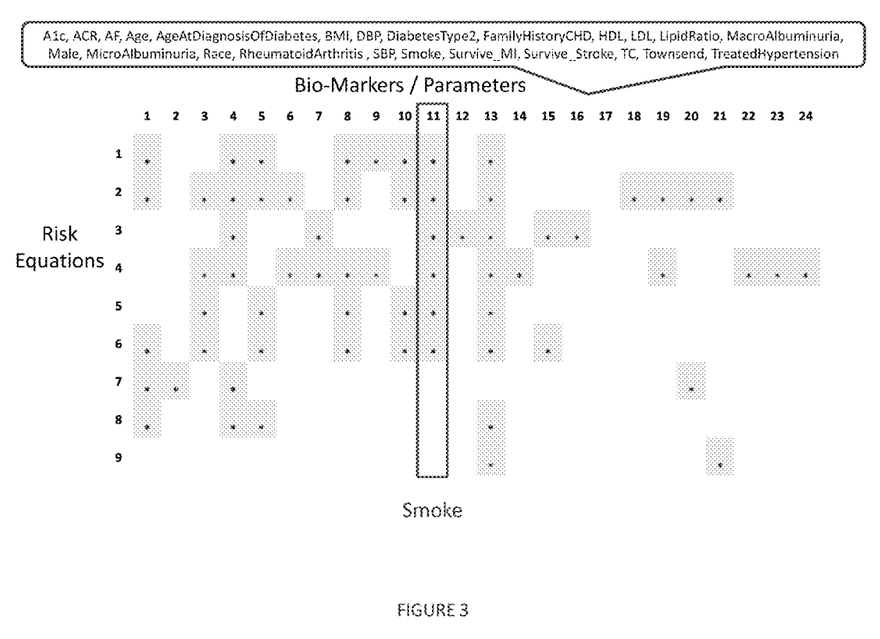
FIG. 3 depicts the parameters used in risk equations which have been published previously which are fed into The Reference Model.

FIG. 3 is a depiction of the biomarkers/parameters used in equations which represent observed phenomena and can be combined with the hypothesis and can be used in The Reference Model. In this example, it is easy to see that risk equations are different and therefore when applied to different cases will produce different results. This shows the motivation and the need for model comparison.

Figure 4:
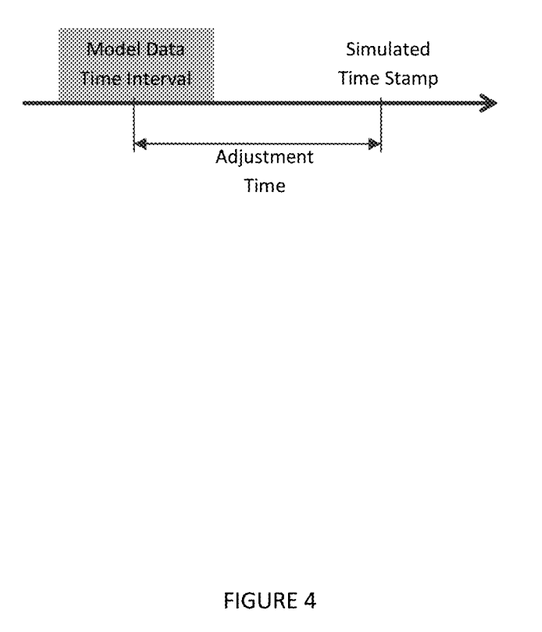
FIG. 4 depicts the correction term.

FIG. 4 is a depiction of the correction term which accounts for model outdate and in the particular parameters of the study used in this example of The Reference Model. In this case, the parameters are adjusted for time past between; model year=average of model data time interval, and simulated time stamp=simulated study year/s.

Figure 5:
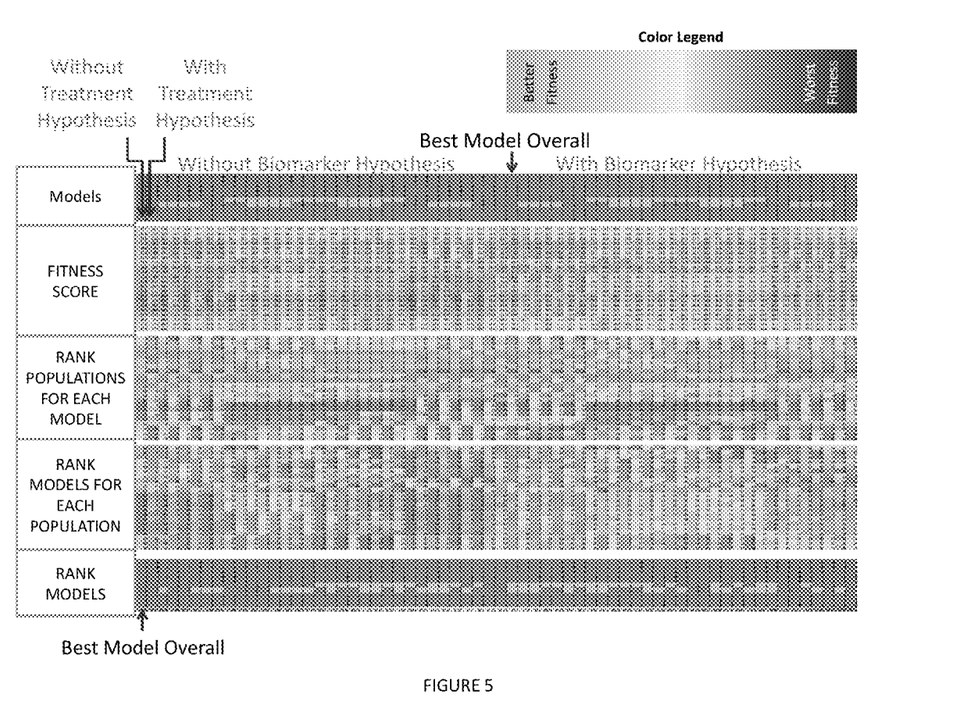
FIG. 5 depicts the results of The Reference Model, with the results with and without biomarker hypotheses being depicted.

FIG. 5 is the results of The Reference Model with the results split between results which utilized the biomarker and did not utilize the biomarker hypothesis. Other data depicted are: the fitness score matrix, the rank populations for each model, rank models for each population, the overall rank of models, and a legend that matches fitness to color.

The Reference Model implements a modeling approach that runs multiple models over multiple populations to determine fitness of different equations/hypotheses to different populations;

16=4×4 different published equation combinations were tested, 4 for Myocardial Infarction (MI) and 4 for stroke. These 16 equation combinations were combined with hypotheses regarding treatment improvement and biomarker change to create 64 different model variations. Those 64 model variations were tested against 22 different clinical trial cohorts from diabetic populations. The equations/hypotheses combinations were ranked according to fitness. In summary, there were 64=4×4×2×2 equation/hypothesis variations, 22 cohorts with known outcomes from 4 diabetic populations: UKPDS, ASPEN, ADVANCE, ACCORD, Monte Carlo simulation included 10 repetitions of 1000 individuals for 10 simulation years, overall there were 14080 processes=64×22×10. These results were obtained, in this case, using a single 8 core desktop computer operating for 4 days.

The treatment improvement hypothesis was deduced from and was defined as a constant yearly improvement in the probability of MI, Stroke, Fatal MI, and Fatal Stroke. It was assumed the improvement is the same for every year and for every one of the probabilities. The biomarker change hypothesis used the end of study biomarker values in the equations starting after one year of simulation, whenever those numbers were published.

The fitness score matrix uses color coding and ranking to visually demonstrate the fitness between 4/22 populations/cohorts and 64 combinations of published risk equations and hypotheses. The results show that different combinations of risk equations behave differently on different population cohorts. For each query, the system ranks the models. Models that implement the following two corrections generally behaved better: Temporal correction for treatment improvement; Biomarker change introduced in the first year.

The results suggest that including the treatment improvement hypothesis is beneficial for most models. Out of 32 model variations, 29 model variations that included treatment improvement component performed better than their counterpart without treatment improvement when accounting for all 16 population cohorts. When considering high resolution results of model per specific population, out of 32×16=512 model and population combinations, there were only 103 instances (20.1%) where the treatment improvement hypothesis worsened the fitness to the published results of the clinical trials.

The results suggest that including the biomarker change hypothesis is beneficial for most models. Out of 32 model variations that included the biomarker change hypothesis 28 had superior results to the models without this hypothesis, when considering all populations. The 4 model variations in which biomarker change did not improve results included the treatment improvement hypothesis.

Current published models do not include components to account for future improvement, which is reasonable since past behavior does not guarantee future behavior. Never the less, this causes models to become quickly outdated. Adding a correction for treatment improvement, as depicted in FIG. 4, will keep models up to date and improves their performance. Adding such a component requires calibration and validation. The Reference Model is a good tool for calibration and validation using multiple models and populations.

The Reference Model uses systematic cross validation of models against populations using micro-simulation and relying on computing power; Defining a fitness score to convert multiple outcome differences into a single number; Defining different queries with weights to rank model/population fitness. The methods avoid using restricted individual data and rely on more accessible summary data. Never the less, it is still possible to use proprietary information such as individual data and proprietary risk equations.

The Reference Model is built from publically available data, using MIST (Micro-Simulation Tool)—a Python based modeling framework which is available under General Public License (GPL), and does not require access to proprietary, or individual patient, information. The software uses Monte Carlo simulations that are executed in parallel, and in the data shown in this application, the system can run on a single machine, on a cluster of machines, and on a cluster in the cloud. With the model utilizing computer power/techniques, such as parallel processing/high performance computing, cross validation, competition among alternative equations and/or hypotheses combinations, and ranks results based on fitness via a fitness engine multiple studies can be compared and large amounts of study data, which was inaccessible before, is now available to determine disease progression over large populations comprising large data sets.

More specific details regarding the use of the technique:

A) The Reference Model helps select a suitable Model to specific Population;

When predicting information for a new study with unknown results it is not known what is the best model to use to predict it. However, if baseline characteristics of a target populations are known it is possible to find the populations that resemble that population baseline to deduce the best model.

For example, a clinical trial for a young population of 20 year olds is being considered. The Reference Model is consulted and all its populations are searched to find the closest populations in its characteristics. Without loss of generality let us assume that there are populations of 25, 40, 65 year old in the system with results. In the simplest case the model that proved best fitting to the young 25 year old population will be chosen to predict disease progression in the young 20 year old target population. This simple case can be extended by defining a population distance function. Once such function is defined by the user the distances between base populations are known. This population distance function can be used as a factor when weighting fitness results from multiple populations and studies. This way, the ranking of the best model for the new target population will be based on information from more than a single population and be less sensitive to outliers.

B) The Reference Model allows investigation of different elements in a model/risk equations to figure which are more important;

The Reference Model provides a fitness score for each model built from multiple risk equations. By averaging these fitness scores for all models associated with a specific risk equation it is possible to derive a fitness score for each risk equation.

It is possible to extend this concept beyond a score for a specific risk equation within a model. It is possible to drill down to the level of specific element within a risk equation. Different risk equations are built from different elements, including risk factors such as Age or Blood Pressure, numeric coefficients that specify the magnitudes of these risk factors, and mathematical element such as addition, subtraction, power, log, exp etc.

Once the score of a risk equation is known it is possible to calculate the score for each element in an equation to figure out what element is most important. For example it would be possible to find out the fitness score of Age or Blood pressure by averaging the scores of the risk equations where they participate. This is one way to derive importance of an element in the equation according to the calculated fitness scores. Again, the elements can then be ranked to find out which is most important.

It is also possible to calculate the fitness score for a factor in the risk equation by using the coefficient of the factor as a weight in a weighted average. This way a factor with relatively larger coefficients in a certain equation be more influenced by the score of this equation. To make sure all equations use the same coefficients, a first order Taylor series expansion can be used, or the user can define those weights manually.

In summary, the idea of the fitness score and associated ranking can be associated with a model, a population, an equation within a model, and a factor in an equation, or with other features associated with the model or population.

C) Details regarding Defining the Fitness Function;

The fitness score function that allows comparing different models and populations is user defined and the user can use their own function to define fitness. However some function elements are useful to construct the fitness function and these can be mixed and matched to create useful fitness functions. These elements comprise:

C1) The norm of difference between model and observed study results is perhaps the simplest fitness function.

C2) Dividing the norm by the square root of number of outcomes in the study allows comparing results from multiple studies with different number of outcomes. For example it allows comparing fitness of a study that only observes death to fitness of a study that observes 2 outcomes: death from stroke and stroke. Without this correction, studies with more outcomes will be less fit just because they have more outcomes. This correction makes studies with a difference of 1 individual in all outcomes equivalent.

C3) Weighing differences between model and observed study results allow the user to emphasize the importance of each specific outcome with a weight. For example it allows the user do emphasize the weight of a stroke or the weight of a death from stroke to be more important than that of Death from other causes.

C4) Providing default study results if undefined by the study. If a study does not measure a result in a population the system can provide a default number. This default number can be based on other studies, previous statistics, or human assessment.

Combining these elements together in various combinations can create different fitness functions that can provide a different views on fitness.

The Reference Model provides a birds eye view of clinical trials, allowing the results from multiple trials to be systematically compared, while at the same time, not requiring the use of proprietary data and allowing the accumalation of knowledge for competition.

The Reference Model is a MultiScale Model that allows combining information from different scales: 1) Individual patient level 2) Study summary information 3) Multi study level; while providing a birds eye view at the Multi-study level. Combining multiple populations/models/hypothesis/outcomes, the Reference Model integrates a map that shows our current understanding of phenomena observed in studies.

The multi scale model allows using only available summary information to derive results and once individual data become available it is possible to increase resolution and use individual data and compare results to the summary data.

The Reference Model allows querying the results of multiple phenomenon in multiple trials using a user defined metric in a unified fashion. This query can be defined visually as a table that is easier to grasp than a textual querying language such as SQL, with the table including: query keys for grouping, study information, and weights for averaging.

Bounds can be used to figure out fitness ranges if information is unknown. For example, if correlation between population parameters such as Blood Pressure and Cholesterol level are unknown, it is possible to define bound populations with no correlation and a population with fully correlated population to deduce the fitness range between those bounding populations.

Throughout this application, various Patents and Applications are referenced by number and inventor. The disclosures of these documents in their entireties are hereby incorporated by reference into this specification in order to more fully describe the state of the art to which this invention pertains.

The foregoing description of the embodiment has been provided for purposes of illustration and description, and is not intended to be exhaustive or to limit the disclosure. Individual limits or features of a particular embodiment are generally not limited to that particular; but, where applicable, are interchangeable and can be used in a selected embodiment, even if not specifically shown or described. The same may also be varied in many ways while such variations are not to be regarded as a departure from the disclosure, and all such modifications are intended to be included within the scope of the disclosure.

I claim:

1. A computer-implemented method comprising:
    obtaining data of a plurality of studies that are associated with a plurality of populations, the data being related to a disease;
    determining, from first results of a first study of the plurality of studies, a first equation to model a progression of the disease, the progression of the disease including a plurality of disease states;
    determining, from second results of a second study of the plurality of studies, a second equation to model the progression of the disease;
    producing a query to determine a fitness of a model to evaluate the progression of the disease in a population of the plurality of populations, the model including the first equation and the second equation;
    performing, using a plurality of processors, a first plurality of simulations to evaluate the progression of the disease based at least partly on the first equation and additional data of individuals included in the population, wherein at least a portion of the first plurality of simulations are performed in parallel;
    performing, using the plurality of processors, a second plurality of simulations to evaluate the progression of the disease based at least partly on the second equation and additional data of individuals included in the population, wherein at least a portion of the second plurality of simulations are performed in parallel;
    determining first differences by comparing first outcomes of the first plurality of simulations and observed outcomes derived from the data of the plurality of studies;
    determining second differences by comparing second outcomes of the second plurality of simulations and the observed outcomes;
    determining a score for the model based at least partly on the first differences and the second differences, the score indicating the fitness of the model to evaluate the progression of the disease in the population;
    ranking by a fitness engine the model with respect to a plurality of additional models based at least partly on the score for the model and individual scores of each model of the plurality of additional models; and
    storing a fitness matrix in memory of a computing device the fitness matrix indicating the score of the model and the individual scores of each model of the plurality of additional models.

2. The method as recited in claim 1, further comprising:
    determining an additional population for a study related to the disease;
    determining a population of the plurality of populations that corresponds with the additional population; and
    determining a population distance function indicating a difference between individuals included in the population and additional individuals included in the additional population for a set of characteristics of the individuals and the additional individuals.

3. The method as recited in claim 2, wherein:
the set of characteristics includes age;
the population distance function indicates differences in the ages of individuals included in the population and the additional population; and
the method further comprising: determining an additional score for the model for the additional population based at least partly on the first differences, the second differences, and the population distance function.

4. The method as recited in claim 1, wherein the first equation includes elements corresponding to risk factors for the disease and coefficients indicating magnitudes of the risk factors.

5. The method as recited in claim 4, further comprising:
identifying a risk factor of the disease;
identifying a first element of the first equation that corresponds with the risk factor; and
identifying a second element of the second equation that corresponds with the risk factor.

6. The method as recited in claim 4, further comprising:
determining a first coefficient of a first element in the first equation, wherein the first element corresponds with a risk factor for the disease; and
determining a second coefficient of a second element in the second equation, wherein the second element corresponds with the risk factor.

7. The method as recited in claim 6, further comprising:
determining a weighted average of the first score and the second score based at least partly on the first coefficient and the second coefficient; and
determining an additional score for the risk factor based at least partly on the weighted average of the first score and the second score.

8. The method as recited in claim 1, wherein the first study has a first number of categories of the observed outcomes; and
wherein the second study has a second number of categories of the observed outcomes that is different from the first number of categories of the observed outcomes.

9. The method as recited in claim 8, further comprising:
determining a first norm with respect to the first differences;
determining a first additional score for the first equation by dividing the first norm by a first square root of the first number of categories of the observed outcomes;
determining a second norm with respect to the second differences; and
determining a second additional score for the second equation by dividing the second norm by a second square root of the second number of categories of the observed outcomes.

10. The method as recited in claim 9, wherein the query is provided as a table.

11. A system comprising:
a plurality of processors; and
non-transitory memory including computer-readable instructions that, when executed by the plurality of processors, perform operations comprising:
obtaining data related to a disease for a plurality of populations;
determining a first equation to model a progression of the disease, the progression of the disease including a plurality of disease states;
determining a second equation to model the progression of the disease;
performing a first plurality of simulations to evaluate the progression of the disease based at least partly on the first equation and the data related to the disease for the plurality of populations, wherein at least a portion of the first plurality of simulations are performed in parallel;
performing a second plurality of simulations to evaluate the progression of the disease based at least partly on the second equation and the data related to the disease for the plurality of populations, wherein at least a portion of the second plurality of simulations are performed in parallel;
determining first differences between the first plurality of simulations and observed outcomes derived from the data related to the disease for the plurality of populations;
determining second differences between the second plurality of simulations and the observed outcomes;
determining a first score for the first equation based on the first differences, the first score indicating a first fitness of the first equation to evaluate the progression of the disease in the plurality of populations;
determining a second score for the second equations based on the second differences, the second score indicating a second fitness of the second equation to evaluate the progression of the disease in the plurality of populations;
ranking the first equation and the second equation based at least partly on the first score and the second score; and
storing a fitness matrix in the non-transitory memory, the fitness matrix indicating the first score and the second score.

12. The system as recited in claim 11, wherein the operations further comprise producing a graphical user interface including a table that includes the first score and the second score.

13. The system as recited in claim 12, further comprising a computing device to display the graphical user interface, and wherein at least a portion of the plurality of processors are located remotely from the computing device in a cloud computing environment.

14. The system as recited in claim 11, wherein the data related to the disease for the plurality of populations includes a study, and wherein the operations further comprise:
determining a correction term estimating improvement for treatment of the disease from a first period of time to a second period of time, the first period of time being related to a date during which the study was conducted and the second period of time being related to an additional date of a simulated study;
performing a third plurality of simulations to evaluate the progression of the disease based at least partly on the first equation, the data related to the disease for the plurality of populations, and the correction term, wherein at least a portion of the third plurality of simulations are performed in parallel; and
performing a fourth plurality of simulations to evaluate the progression of the disease based at least partly on the second equation, the data related to the disease for the plurality of populations, and the correction term, wherein at least a portion of the fourth plurality of simulations are performed in parallel.

15. A computer-implemented method comprising:
obtaining data related to a disease for a plurality of populations, wherein the disease is associated with a plurality of states;
producing a query to determine scores for a plurality of models with respect to the data related to the disease for the plurality of populations, wherein individual models of the plurality of models include one or more equations that model a progression between at least two states of the plurality of states of the disease;
performing, using a plurality of processors, a plurality of simulations for each of the plurality of models to evaluate the progression of the disease based at least partly on the data related to the disease from a plurality of populations, wherein at least a portion of the plurality of simulations are performed in parallel;
determining differences between outcomes of the plurality of simulations and observed outcomes derived from the data related to the disease for the plurality of populations;
determining individual scores for each model of the plurality of models based at least partly on the differences, the individual scores indicating a fitness of a model of the plurality of models to evaluate the progression of the disease for a population of the plurality of populations;
ranking the plurality of models based at least partly on the individual scores; and
storing a fitness matrix in memory of a computing device, the fitness matrix indicating the individual scores for each model of the plurality of models.

16. The method as recited in claim 15, further comprising:
determining additional individual scores for each population of the plurality of populations based at least partly on the differences; and
ranking the plurality of populations based at least partly on the additional individual scores.

17. The method as recited in claim 15, wherein the method further comprises:
obtaining additional data related to a hypothesis to test;
performing, using the plurality of processors, a plurality of additional simulations for each of the plurality of models to evaluate the progression of the disease based at least partly on the data related to the disease from a plurality of populations and the additional data related to the hypothesis, wherein at least a portion of the plurality of simulations are performed in parallel;
determining additional differences between the plurality of additional simulations and the observed outcomes;
determining individual additional scores for each model of the plurality of models based at least partly on the additional differences; and
ranking the plurality of models based at least partly on the individual additional scores.

18. The method as recited in claim 17, wherein an individual additional score for a model of the plurality of models is improved in relation to an individual score for the model.

19. The method as recited in claim 15, wherein a first model of the plurality of models includes a group of equations to evaluate the progression of the disease for a first population and a second model of the plurality of models includes the group of equations to evaluate the progression of the disease for a second population, and wherein a first individual score indicates a first fitness of the first model to evaluate the progression of the disease for the first population and a second individual score indicates a second fitness of the first model to evaluate the progression of the disease for the second population.

20. The method as recited in claim 15, wherein a first model of the plurality of models includes a first group of equations to evaluate the progression of the disease for a population and a second model of the plurality of models includes a second group of equations to evaluate the progression of the disease for the population, the second group of equations being different from the first group of equations, and a first individual score indicates a first fitness of the first model to evaluate the progression of the disease for the population and a second individual score indicates a second fitness of the second model to evaluate the progression of the disease for the population.

* * * * *